United States Patent [19]
MacPherson et al.

[11] Patent Number: 6,111,161
[45] Date of Patent: *Aug. 29, 2000

[54] PROCESS FOR PRODUCTION OF PARAXYLENE COMPRISING A HIGH-TEMPERATURE CRYSTALLIZATION WITH AT LEAST ONE STAGE AND A PARTIAL MELTING OF THE CRYSTALS

[75] Inventors: Stuart R MacPherson, Piedmont, Calif.; Paul Mikitenko, Noisy le Roy, France

[73] Assignee: Institute Francais du Petrole, France

[ * ] Notice: This patent is subject to a terminal disclaimer.

[21] Appl. No.: 08/875,278

[22] PCT Filed: Jan. 17, 1996

[86] PCT No.: PCT/FR96/00078

§ 371 Date: Jul. 21, 1997

§ 102(e) Date: Jul. 21, 1997

[87] PCT Pub. No.: WO96/22262

PCT Pub. Date: Jul. 25, 1996

[30] Foreign Application Priority Data

Jan. 20, 1995 [FR] France ................................. 95 00746

[51] Int. Cl.⁷ .................. C07C 7/14; C07C 5/22
[52] U.S. Cl. .................. 585/812; 585/813; 585/814; 585/815; 585/479
[58] Field of Search ................... 585/812, 813, 585/814, 815, 479

[56] References Cited

U.S. PATENT DOCUMENTS

| | | | |
|---|---|---|---|
| 5,284,992 | 2/1994 | Hotier et al. | 585/805 |
| 5,329,060 | 7/1994 | Swift | 585/805 |
| 5,329,061 | 7/1994 | Swift . | |
| 5,401,476 | 3/1995 | Hotier et al. | 422/221 |
| 5,659,098 | 8/1997 | Beck et al. | 585/475 |
| 5,866,740 | 2/1999 | Mikitenko et al. | 585/470 |

*Primary Examiner*—Marian C. Knode
*Assistant Examiner*—Thuan D. Dang
*Attorney, Agent, or Firm*—Millen, White, Zelano & Branigan, P. C.

[57] ABSTRACT

A process for production of paraxylene from a charge containing C7–C9 aromatic hydrocarbons in which a first fraction is enriched to at least 30% weight with paraxylene and this fraction is purified by at least one high-temperature crystallization in at least one crystallization zone. Said first fraction is crystallized in a crystallization zone at high temperature T1 and advantageously between +10 and −25° C., crystals in suspension in a mother liquor are recovered, the crystals are separated from the mother liquor in at least a first separation zone, the crystals obtained are partially melted in at least a zone for partial melting and a suspension of crystals is recovered, the crystals in suspension are separated and washed in at least one separation and washing zone and pure paraxylene crystals and washing liquor are recovered, and pure crystals are optionally completely melted and a liquid stream of melted paraxylene is collected.

32 Claims, 3 Drawing Sheets

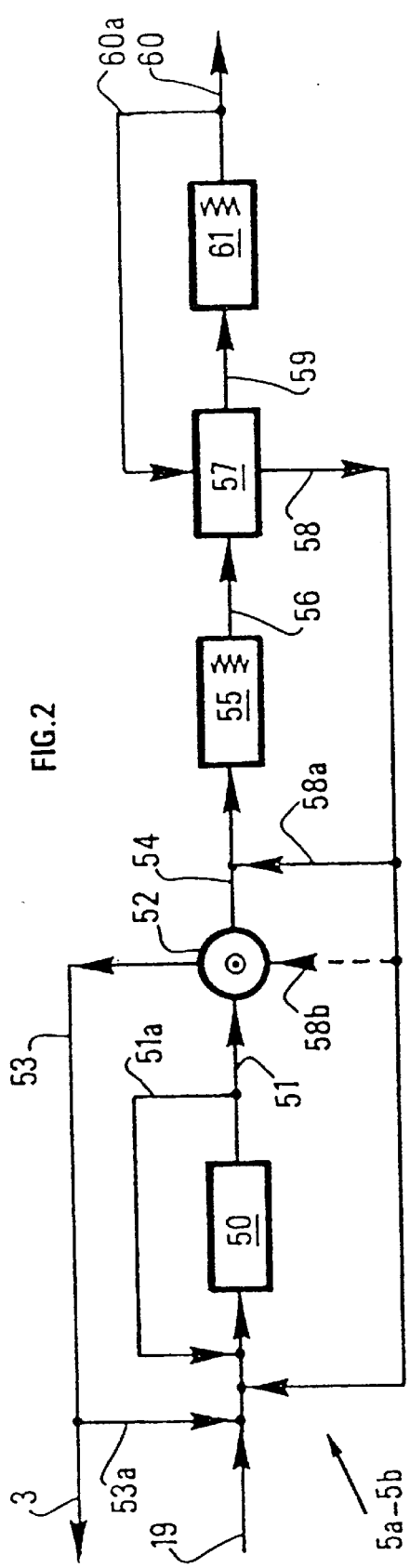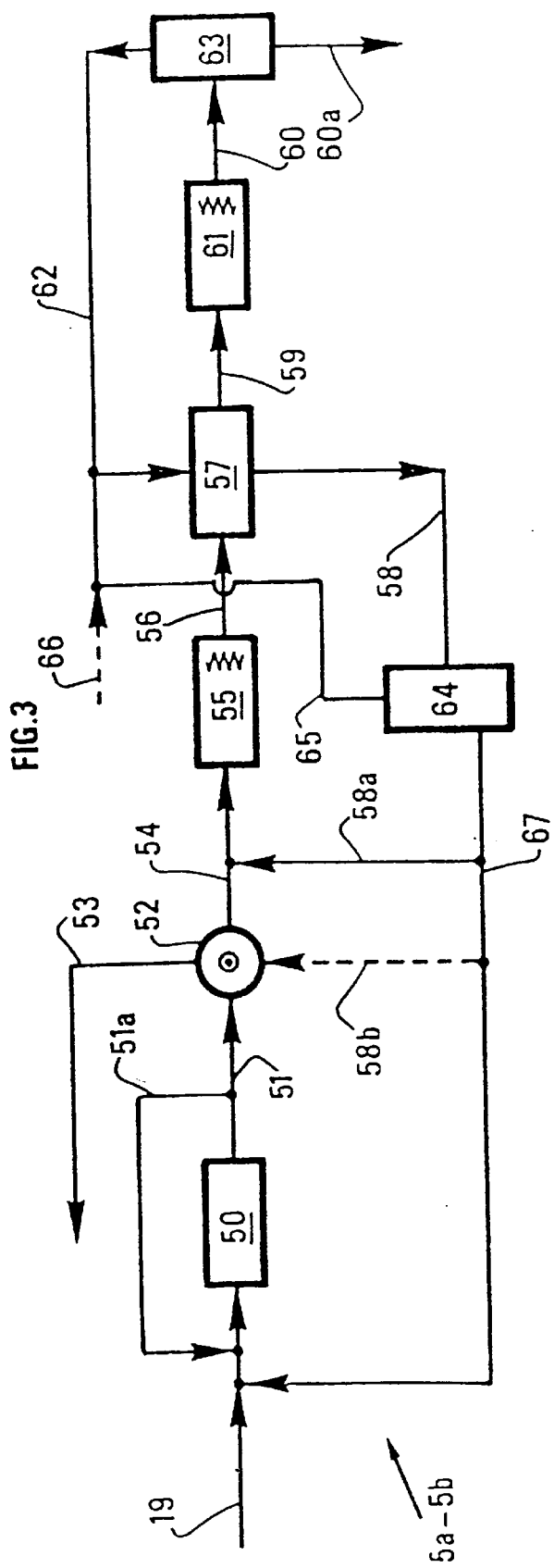

PROCESS FOR PRODUCTION OF PARAXYLENE COMPRISING A HIGH-TEMPERATURE CRYSTALLIZATION WITH AT LEAST ONE STAGE AND A PARTIAL MELTING OF THE CRYSTALS

BACKGROUND OF THE INVENTION

The invention relates to a new economic process for recovering and purifying paraxylene from a charge of hydrocarbons which contain paraxylene at a concentration that is greater than that at thermodynamic equilibrium. It relates, in particular, to the processes that enrich their effluent with paraxylene to more than 30%, particularly the processes that provide at least one paraxylene-enrichment step by crystallization at very low temperature, for example, this crystallization step being followed by a step of purifying the paraxylene in at least one stage (U.S. Pat. No. 3,177,265 and U.S. Pat. No. 2,866,833).

The invention relates in particular to a process for preparing and purifying paraxylene from a charge of aromatic hydrocarbons having 8 carbon atoms comprising a combination of steps for selective adsorption, for purification by high-temperature crystallization and for isomerization as described in the patents of the applicant FR 2,681,066 and U.S. Pat. No. 5,284,992 that are incorporated by reference.

It applies in particular to the preparation of paraxylene with very high purity for the production of terephthalic acid for the synthesis of synthetic fabrics.

Crystallization has been used commercially for a very long time to isolate and purify paraxylene, typically from a mixture of xylenes and ethylbenzene close to equilibrium ($C_8$-aromatic fraction).

The $C_8$-aromatic fractions ordinarily come from a reforming unit or from an ethylene production unit and especially from the reformates by distillation alone or extraction in combination with a distillation as a function of the composition of the charge, of the sensitivity to impurities of the downstream technologies and of the savings of the recovery processes.

The typical composition by weight of a $C_8$-aromatic fraction is approximately 22% paraxylene, 16% ethylbenzene, 18% orthoxylene and 44% metaxylene. Very low temperatures are generally required to effectively recover, by crystallization, the paraxylene from a $C_8$ fraction. Furthermore, there is a eutectic limit that prevents the complete recovery of all the paraxylene from a $C_8$ fraction. For example, in a low-temperature crystallization unit, for a $C_8$-aromatic fraction containing 22% weight of paraxylene, only about 50 to 65% of the paraxylene is recovered, the remaining paraxylene will be found in the paraxylene-depleted mother liquor, which can be introduced into an isomerization unit. The latter will isomerize the metaxylene, orthoxylene and in certain processes, the ethylbenzene, and a mixture of xylenes close to equilibrium containing about 22% paraxylene will again be obtained. This recycled flow, in combination with the fresh charge, is then introduced into the crystallizer so as to recover more paraxylene. In this way, the $C_8$-aromatics can be recycled to extinction and recovery of a maximum amount of paraxylene, with by-products resulting from the isomerization. The production of these by-products is a significant insufficiency of the system since each time that xylenes are introduced into the isomerization unit, a part of them is converted into non-xylenes such as toluene. Actually, the chemistry of the isomerization is very complex and the main reactions which lead to losses of xylenes are the disproportionation (dismutation) of the xylenes into toluene and trimethylbenzenes, dealkylation of the xylenes, and in certain cases even the formation of non-aromatics. To do this, the total yields of a set of isomerization and crystallization units are typically 60 to 80% and a large isomerization recycling loop is necessary to maximize the recovery of the paraxylene.

In the 1970's, another process was marketed to prevent the eutectic limitation from a low-temperature crystallization. This process uses an adsorption to separate the paraxylene from a mixture of xylenes. The adsorption makes it possible to recover more paraxylene from a $C_8$-aromatic fraction. Thus, from a charge containing 22% weight of paraxylene, it is possible to recover approximately 97% of the latter by adsorption, leaving about 1% paraxylene in the mother liquor. It is advantageous to recover the product with a greater efficiency, since this entails the use of a much smaller isomerization loop for the complete recycling of the paraxylene-depleted fraction. This offers several advantages, particularly a lower investment cost on a new unit or on the expansion of an existing unit, overall higher yields due to low losses in isomerization, and lower operating costs linked to the size of the isomerization loop.

Several drawbacks linked to the system for recovery by adsorption of paraxylene are noted, however: high investment cost, difficulty in obtaining paraxylene with very high purity, sensitivity of the adsorbent to impurities in the charge and sensitivity of the control system to changes in quality of the charge.

Furthermore, a process for crystallization that uses two separate crystallization stages (AMOCO process) has been proposed. Demand for a higher purity of paraxylene was increasingly difficult to satisfy by a single crystallization. A process was therefore developed which completely remelts the crystals that were isolated from the first crystallization stage at very low temperature. After complete remelting, the flow was cooled to about −17° C. to recrystallize the paraxylene to the desired purity. This process was able to deliver high purities (99.5%+) after washing. However, it has the drawback of higher operating and investment costs due to the cost of the energy associated with a complete remelting and then to a recrystallization of the paraxylene.

A process of the applicant has recently been patented, which combines in particular an adsorption with a crystallization; it is patent U.S. Pat. No. 5,284,992 which describes a selective adsorption to recover the paraxylene from a charge containing a mixture of xylenes. The paraxylene is then purified by at least a high-temperature crystallization. It is taught that there is a synergy between the adsorption and the high-temperature crystallization, due to the fact that the adsorption is a very efficient process for recovering paraxylene from xylenes and that the crystallization is a very efficient means for purifying paraxylene to a very high level, which constitutes an ideal link between the two technologies. Moreover, this process emphasizes the full advantage of a smaller isomerization loop due to an almost quantitative recovery by pass of the paraxylene into the adsorption step of the unit.

Another patent U.S. Pat. No. 5,329,060 teaches a process comprising a selective adsorption step of a charge of a mixture of xylenes followed by a double-stage crystallization of paraxylene, one at very low temperature (−50 to −70° C.) and the other at high temperature (0 to −10° C.). The operating and investment cost of this process is all the higher since it provides a crystallization at very low temperature and a complete melting of the crystals obtained before their recrystallization.

Moreover, in the sequence of steps comprising an adsorption, a crystallization and especially an isomerization, to obtain very pure paraxylene, various types of impurities can appear in the various effluents and cause disturbances in the operation of units thus interfering with the yield obtained and the purity of the paraxylene recovered.

First, during isomerization of the paraxylene-depleted fraction, olefinic hydrocarbons can be produced in a variable amount depending on the values of the partial pressures of hydrogen introduced. The subsequent formation of polymers before and/or in the adsorption unit can cause serious problems with circulation through the adsorbent, and even destroy the adsorbent. Moreover, paraffinic and naphthenic hydrocarbons with 8 and 9 carbon atoms, whose volatility is between that of, a desorption solvent, for toluene, and that of the xylenes, are intermediate products of the conversion of ethylbenzene into xylenes during the isomerization and their accumulation can prove to be harmful. Furthermore, aromatic hydrocarbons with 9 carbon atoms and more, present in small proportion and poorly separated in distillation columns, can be detrimental to the process, just like aldehydes and ketones that are heavier than the initial charge, which are formed when oxygen is accidentally dissolved.

Finally, another problem is linked to the presence of methanol. This alcohol is at times added in small proportion in mixtures of xylenes to be crystallized to prevent the co-crystallization of water and of paraxylene. Actually, the mixtures of dry $C_8$-aromatics are particularly hygroscopic and when the suspension of paraxylene crystals in the mother liquor passes into the centrifuge, water contained in the ambient air can be absorbed in the mother liquor and this water can possibly crystallize in connection with the temperature of this mother liquor. Moreover, some exchangers can have leaks and water can pass accidentally into the mixture to be crystallized.

SUMMARY OF THE INVENTION

An object of the invention is to produce paraxylene with the highest possible purity with a greater flexibility and at the most economical cost possible.

Another object is to eliminate the drawbacks mentioned.

A further object is to limit the amount of the impurities, particularly in the adsorption section, to try to optimize it, to the extent that the adsorbent is very sensitive to the impurities of the charge of the adsorption zone.

It has therefore been observed that by using a high-temperature crystallization in a single stage, or advantageously a high-temperature crystallization in several stages and preferably in two stages followed by a partial melting of the recovered crystals, a process was obtained with a better recovery of paraxylene and also very economical especially since the cooling fluids used are easy to use. Furthermore, the risk of increasing the concentration of undesirable impurities in the effluents is minimized.

More specifically, the invention relates to a process for the production of paraxylene of very high purity from a charge containing a mixture of aromatic hydrocarbons having 7 to 9 carbon atoms in which at least a part of the charge is circulated in a zone suited to enrich a first fraction to at least 30% by weight of paraxylene, and at least a portion of said first fraction is purified by at least one high-temperature crystallization in at least one crystallization zone, the process being characterized in that:

a) said first fraction enriched with paraxylene is crystallized in a crystallization zone at high temperature T1 and advantageously, between +10 and −25° C., b) crystals in suspension are recovered in a mother liquor, c) the crystals of the mother liquor are separated in at least a first separation zone, preferably at a temperature that is approximately constant and approximately equal to that of crystallization T1, d) the crystals of step (a) are partially melted in at least a partial melting zone and a suspension of crystals is recovered;

e) the crystals in suspension of step (d) are separated and washed with a suitable washing solvent in at least one zone for separating and washing, and, on the one hand, pure paraxylene crystals, and, on the other hand, a washing liquor are recovered; and f) said pure crystals are optionally completely melted and a liquid stream of melted paraxylene is collected.

The washing step can include pure paraxylene liquid product.

By high-temperature crystallization is meant a crystallization in at least one crystallizer for each crystallization stage of a solution or suspension of paraxylene, already enriched with paraxylene, which corresponds to what the literature calls a purification step. For example, U.S. Pat. No. 2,866,833, incorporated as a reference, mentions a step of purifying paraxylene at high temperature able to go up to a temperature of −34° C.

By carrying out a step of partial melting of the crystals, the surface impurities are in part eliminated, the crystals of small size are melted, and the temperature of the crystals is increased which makes possible an efficient operation of the means for separating and for washing the paraxylene crystals mentioned below, and consequently for achieving very high purities. The heat input necessary for the partial melting can be performed in the partial melting zone itself and/or upstream from it, thanks, for example, to the recycling of at least a portion of the optionally heated washing liquor.

According to a first variant, the enrichment zone of the first fraction with at least 30% by weight of paraxylene can be at least one crystallization zone at very low temperature, for example, lower than −40° C., said recovery section, such as the one described in U.S. Pat. No. 2,866,833 or such as those described in U.S. Pat. No. 5,329,061 that are incorporated by reference and in which a charge containing aromatic hydrocarbons having 8 carbon atoms is introduced. This enrichment zone delivers a suspension of crystals which is separated in a separation zone and the recovered crystals are melted and constitute at least a part of said first fraction to be purified later on. Moreover, a mother liquor resulting from the separation can be isomerized in an isomerization zone and the isomerate at least in part recycled to the enrichment zone (recovery section).

According to a second variant, the paraxylene-enrichment zone can be a selective adsorption zone containing a zeolitic adsorbent and in which a charge containing aromatic hydrocarbons having 8 carbon atoms is introduced. A selective adsorption of the charge is carried out, in the presence of a desorption solvent, said first paraxylene-enriched fraction and a second paraxylene-depleted fraction are recovered, said second fraction is isomerized in an isomerization zone containing a catalyst for isomerization under conditions suitable for producing an isomerate containing paraxylene approximately at thermodynamic equilibrium with isomers and the isomerate is recycled at least in part to the adsorption zone.

The desorption solvent is generally selected as a function of the nature of the adsorption. By way of example, it is possible to use toluene, paradiethylbenzene, difluorobenzene, diethyl toluene, or an alkyltetraline, particularly described in U.S. Pat. No. 4,886,929, U.S. Pat. No. 4,864,069, and U.S. Pat. No. 5,057,643 which are incorporated by references.

According to a third variant the paraxylene enrichment zone can be a disproportionation zone of a charge consisting essentially of toluene and using a coke-selectivated catalyst or a silicon-selectivated catalyst according to U.S. Pat. Nos. 4,117,026, 4,097,543, 4,851,604, 5,173,461, 5,243,117 and U.S. Pat. No. 5,321,183, incorporated by reference.

The unreacted toluene and the benzene are advantageously removed by distillation from the disproportionation effluent comprising the xylenes.

It is advantageous to have an effluent containing more than 50% by weight of paraxylene and preferably 75 to 98% coming out of the enrichment zone, i.e. for example of the selective adsorption zone as described in U.S. Pat. No. 5,284,992 of the applicant.

At least a portion of the mother liquor resulting from a separation step after the one-stage high-temperature crystallization of the charge of hydrocarbons can be recycled to the enrichment zone, for example to the adsorption zone. This separation step can be carried out by at least one centrifuge or at least one rotary filter, which are means known to one skilled in the art.

In the same way, the step of separating and washing crystals, which is carried out in the same zone, after the step of partial melting, can be performed in at least one centrifuge or one rotary filter. According to a preferred variant, it can be carried out in a zone for separating and washing where the washing solvent is introduced countercurrent to the paraxylene crystals to be washed as described in U.S. Pat. No. 4,475,355, U.S. Pat. No. 4,481,169 and CH 515,730 that are incorporated by references. More specifically, this zone for separating and washing can comprise at least one washing column, such as a NIRO column.

The resulting washing liquor, optionally distilled if necessary, can be advantageously recycled at least in part in the crystallization zone, a portion being able to be sent to the partial melting zone to keep the proportion of crystals at a suitable level.

However, when the zone for separating and washing is a centrifuge, it is also possible to recycle a portion of the washing liquor in the separation zone coming out of the crystallization stage, which makes it possible to have a better purity of the final paraxylene.

According to another particularly advantageous embodiment making it possible to reduce the operating cost of the process, it is possible to perform the purification of the paraxylene in at least two crystallization stages at high temperature T1 and T2 and preferably between +10 and −25° C. In this case, steps a, b, c and d described above are carried out, at least a portion of the mother liquor resulting from step c) is crystallized in a second crystallization zone at a high temperature T2 that is lower than temperature T1 of the crystallization zone of step a), second crystals in suspension are recovered in a second mother liquor, said second crystals of said second mother liquor are separated in a second separation zone, the second crystals are melted partially in at least one zone for partial melting, a suspension of said first crystals resulting from step d) and second crystals are recovered, the crystals obtained are separated and washed in at least one zone for separating and washing with the washing solvent, pure paraxylene crystals, on the one hand, and a washing liquor, on the other hand, are recovered, and optionally said pure crystals are completely melted, then the liquid stream of melted paraxylene is collected.

It is possible to recycle at least a portion of the washing liquor in the first crystallization zone, another portion being able to be recycled to the partial melting zone, which recovers the crystals of two crystallization zones so as to maintain a concentration of crystals of about 35% by weight, for example, in this tank.

As has been stated above, the step of separating and washing the crystals after the step of partial melting can be carried out either in at least one countercurrent washing column, or in at least one centrifuge or one rotary filter. All of the crystals in suspension can be separated and washed in the same element or else the first crystals in suspension can be separated and washed in at least one column, one centrifuge or one rotary filter and the second crystals in suspension can be separated and washed in at least one separate column, one separate centrifuge or one separate rotary filter. In the case of washing by at least one centrifuge or one rotary filter, it is possible to recycle a portion of the washing liquor in the first separation zone following the first crystallization stage and optionally a portion of the washing liquor in the second separation zone coming out of the second crystallization stage.

According to a characteristic of the process preferably comprising two crystallization stages, at least a portion of the mother liquor coming out of the second separation zone can be recycled to the enrichment zone, and more specifically to the selective adsorption zone.

It can be particularly advantageous to maintain a certain amount, about 30% by weight, for example, of crystals in the first crystallization effluent and in the second crystallization effluent. For this purpose, it is possible to recycle a portion of the first mother liquor in the first crystallization zone and a portion of the second mother liquor in the second crystallization zone. The temperature and the proportion of crystals in each crystallizer thus are controlled independently.

It has been observed that by operating at a first crystallization temperature T1 advantageously between +10 and −5° C., and preferably between +5 and −1° C., and at a second crystallization temperature T2 between −5 and −25° C. and preferably between −9 and −25° C., excellent results are obtained, the temperature selected depending on the type of cooling agent, on the optimization between the enrichment steps, for example, by adsorption, the crystallizations and the final washing.

According to a characteristic of the process, the final washing of the paraxylene at the end of the process, carried out in at least one centrifuge or one rotary filter or in at least one countercurrent washing column, a NIRO column for example, can be performed by a portion of the liquid stream of pure paraxylene coming from the complete melting step, which is used as washing solvent.

According to another characteristic of the process, the final washing of the paraxylene at the end of the process, carried out in at least one centrifuge or one rotary filter or in at least one countercurrent washing column, a NIRO column for example, can be performed by a washing solvent which is a solvent other than paraxylene, toluene, hexane or pentane for example. In this case, the stream of melted paraxylene is distilled, there is recovered, on the one hand, paraxylene of very high purity, and, on the other hand, washing solvent that is recycled at least in part in the zone for separating and washing, the washing liquor that contains washing solvent in a small amount is also distilled, and at least a portion of the washing solvent that is distilled in this way is recycled in the zone for separating and washing.

When the operation is with a countercurrent washing column, and a solvent other than paraxylene, it can be advantageous to separate the suspension of paraxylene-crystals coming from this column by a filter or a centrifuge, before the melting step of the paraxylene and to recycle the solvent separated in this way in the washing column.

The washing liquor, after distillation, is then generally recycled as indicated above.

The partial melting zone is generally effected at a temperature between the temperature of the coldest crystallization stage of the purification zone and the melting temperature of the pure paraxylene, and preferably between 0 and 11° C. to melt, for example, between 5 and 60% by weight of the crystals.

It generally comprises a tank receiving the crystals and heating means, for example by steam.

It is possible to use a single zone for partial melting, which recovers the first and second crystals.

However, it can prove preferable to melt partially the first and the second crystals which have a different degree of purity in two separate zones. In this case, the recycling of the washing liquor can be envisioned in each of the two zones to maintain the proportion of crystals at a suitable level.

The process according to the invention makes it possible to obtain paraxylene of very high purity.

It has been observed, however, that it was possible to improve the performances of the equipment by controlling at all levels the proportion of impurities that can disturb the selective adsorption of the paraxylene on the absorbent and its crystallization, whether at the level of the charge of aromatic hydrocarbons, the isomerate and/or the recycled mother liquor. (Patent application of the applicant No. 94/15,896.)

More generally, it is possible to circulate a portion selected from at least in part the charge, at least in part the mother liquor, at least in part the isomerate in at least one treatment zone with clay or equivalent material, and a first effluent is recovered that is introduced at least in part in the adsorption zone or in the very low temperature crystallization zone.

According to the variant comprising a purification with a crystallization stage, it is possible to circulate respectively the mother liquor resulting from the separation step in at least one clay treatment zone before recycling it in the enrichment zone, in particular in the adsorption zone or in the very low temperature crystallization zone.

According to the variant comprising a purification with two crystallization stages, the second mother liquor resulting from the separation of the crystals coming out of the second crystallization zone is introduced into the clay treatment reactor.

These clay treatments make it possible to eliminate at least in part the olefins created in particular in the isomerization step and at least a portion of the heavy impurities, which circulate in the enrichment zone, crystallization and isomerization loop.

Various variants can be envisioned:

The mother liquor can be advantageously introduced at least in part into a distillation column, advantageously that downstream from the isomerization zone. This column also treats the effluent of the isomerization zone and delivers a top fraction containing light compounds (water, methanol, $C_7$-) and another fraction containing a distilled mixture of mother liquor and isomerate that is then introduced into the clay treatment zone.

A distillation bottom fraction containing heavy compounds can also be drawn off from this distillation column, which makes it possible to reduce the size of the downstream equipment.

A portion of the mother liquor can also be mixed with the effluent, whatever it is, leaving the clay treatment zone, whether this is the effluent resulting from the circulation of the isomerate, the mother liquor or the charge in the clay treatment zone, or the effluent resulting from the circulation, in the clay treatment zone, of the latter and of the distillation fraction containing said distilled mixture of mother liquor and isomerate, before being introduced into the selective adsorption zone.

The resulting effluent of these latter variants can be distilled in at least one distilling column (a so-called rerun column) which delivers a bottom fraction containing heavy compounds and a top fraction which is introduced into the adsorption zone optionally with a portion of the mother liquor.

The conditions for adsorbing or eliminating undesirable compounds in the clay are, as a general rule, the following:

Temperature: 100 to 300° C., preferably 160 to 230° C.

Hourly space velocity: 1 to 8, preferably 1 to 4 (Hourly volume of charge per volume of clay)

Type of clay; activated natural aluminosilicates, for example, the clay referenced F54 with ENGELHARD.

Pressure: 3 to 100 bar, preferably 4 to 20 bar.

The distillation column, depending on the isomerization, generally has the following characteristics:

Pressure: 1 to 20 bar, preferably 3 to 8 bar

Base temperature: 150 to 280° C., preferably 200 to 240° C.

Number of plates: 30 to 80, preferably 50 to 70.

The distilling column, known as rerun, located between the clay treatment zone and the selective adsorption zone usually has the following characteristics:

Pressure: 1 to 20 bar, preferably 3 to 8 bar bottom temperature: 160 to 290° C., preferably 210 to 250° C.

Number of plates: 40 to 200, most often 50 to 90.

According to another characteristic of the invention, it is possible to keep the amount of constituents with intermediate volatility between that of the desorption solvent and that of paraxylene, at a tolerable level. In this case, at least a portion of the mother liquor can be purged before being introduced into the clay treatment zone.

It can also be advantageous to purge at least in part the desorption solvent resulting from distillation steps of the depleted fraction or of the paraxylene-enriched fraction before it is recycled and to compensate for the purge of the solvent by an addition of fresh solvent, either into the charge or upstream from the adsorption zone, for example.

As has been indicated, it is possible to recycle the crystallization mother liquor in different places of the installation depending on the magnitude of the amounts of undesirable compounds, but it can be advantageous to combine these different recyclings with one another, for example, when it involves reusing existing pieces of equipment for the distillation of the isomerate, the clay treatment or the so-called rerun distillation and when one of these pieces of equipment is already operated at its maximum flow rate.

It is also possible to combine these different recyclings and these purges when it is desired to have the amount of an impurity in the loop reduced without seeking to eliminate it altogether.

BRIEF DESCRIPTION OF THE DRAWINGS

The invention will be better understood in view of the following figures that illustrate in a nonlimiting way several embodiments of the invention, of which:

FIGS. 2 and 3 illustrate the purification of paraxylene by crystallization in a single stage at high temperature respectively comprising a washing by melted paraxylene and toluene.

DETAILED DESCRIPTION OF THE DRAWINGS

Figure 1:
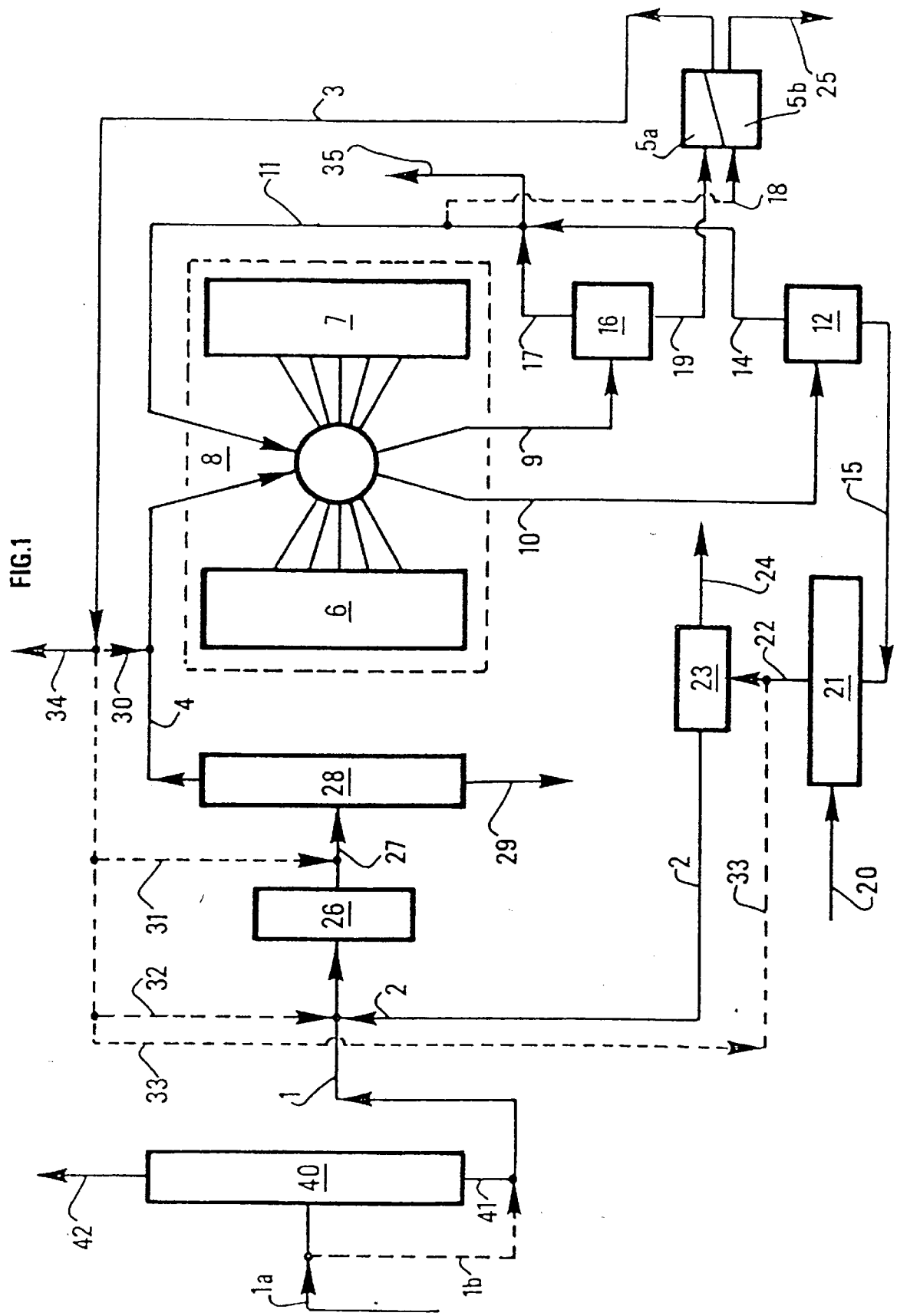
FIG. 1 diagrammatically represents the process, combining an adsorption, a crystallization and an isomerization, as well as treatments upstream from the mother liquor, of the charge and of the isomerate.

By way of example, the paraxylene-enrichment zone consists of a selective adsorption zone on an adsorbent in which the charge of aromatic hydrocarbons with 8 carbon atoms is made to circulate.

The operating conditions of the adsorption in a simulated moving bed (countercurrent, for example) are selected so that the first fraction containing metaxylene, orthoxylene and ethylbenzene is a raffinate and the second fraction containing. essentially paraxylene is an extract. These conditions are described in U.S. Pat. No. 5,284,992 that is incorporated by reference.

By a line 1, a charge is conveyed (FIG. 1) that comprises about 20% ethylbenzene, 18% paraxylene, 45% metaxylene and 17% orthoxylene. Joined to it by a line 2 is a recycled effluent whose ethylbenzene content is appreciably lower, typically 8 to 13%, and which contains impurities. By lines 3 and 30, another recycled effluent is introduced whose paraxylene content is greater, typically 25 to 45%. A line 4 recovers the charge and these two effluents, it conveys a mixture of approximate composition, paraxylene 20 to 22.5, ethylbenzene 9 to 14%, orthoxylene 20 to 22.5%, metaxylene 45 to 50%, which is introduced into a simulated countercurrent adsorption zone 8 comprising one or more columns 6 and/or 7 filled with a zeolitic adsorbent, each of the columns being divided into a limited number of beds, the number of the beds of each column being able to be between 4 and 20, the productivity, expressed in relation to the paraxylene produced, being about 0.07 m$^3$ per m$^3$ of sieve and per hour expressed at ambient conditions. Desorbing is by toluene, at a rate of about 1.45 m$^3$ of toluene per m$^3$ of charge, the operating temperature being approximately 160° C. Drawn off from this unit by a line 10 is a paraxylene-depleted raffinate containing essentially toluene, metaxylene, ethylbenzene and orthoxylene and, by a line 9, an extract of paraxylene-enriched composition containing essentially toluene and paraxylene, the major impurity being ethylbenzene. The raffinate is introduced into a distilling column 12 (top temperature 125° C., bottom temperature 160° C., for example). Drawn off at the top by a line 14 is toluene (about 30% of the amount introduced into the adsorption, for example) containing, for example, less than 2% of C$_8$-aromatic compounds and, drawn off at the bottom of this column by a line 15 is a liquid (raffinate free of solvent) rich in ethylbenzene, metaxylene and orthoxylene and depleted of paraxylene (less than 3%, for example) that is sent into an isomerization unit 21. This raffinate is put in contact with hydrogen introduced by a line 20 and with a catalyst having a base of mordenite and platinum on aluminum at about 380° C. A line 22 conducts the isomerate from the outlet of the reactor to a flask for separating the gaseous constituents (not shown in the figure), then to a distilling column 23 (top temperature 90° C., bottom temperature 160° C., for example). Drawn off at the top by a line 24 are C$_1$ to C$_5$ hydrocarbons, hexane, cyclohexane, benzene and toluene and at the-bottom of this column by a line 2, an effluent containing 8 to 13% ethylbenzene, 21 to 24% paraxylene, 21 to 24% orthoxylene, 45 to 50% metaxylene and impurities, which is recycled to adsorption zone 8.

Line 9 introduces the extract into a distilling column 16 from which toluene having less than 2% C$_8$-aromatic compounds (about 70% of the amount introduced into the adsorption, for example) is drawn off at the top and is recycled by lines 17 and 11 to the feed of desorption solvent of the adsorption unit. At the bottom of column 16 at about 160° C., a stream enriched with paraxylene (at about 90% paraxylene) is drawn off by means of a line 19 which conducts it into a one-stage crystallization unit 5a, 5b, for example operating at about −10° C., from which pure paraxylene is removed by a line 25.

This crystallization unit as well as the means for downstream treatment are represented in FIG. 2.

The crystallization charge at 90% by weight, for example, of paraxylene is introduced by line 19 into at least one crystallizer 50, which generally comprises, upstream from the crystallizer itself, a crystallization charge vat (not shown), into which are introduced the charge and the various recyclings mentioned below.

A suspension of crystals is produced in a mother liquor by a line 51 which is in part recycled to crystallizer 50 by a line 51a, the remaining part being introduced into at least one centrifuge 52 or one rotary filter. A mother liquor is separated from the crystals and recycled at least in part by a line 53 and a line 3 to adsorption unit 8. A portion of this mother liquor can be recycled in crystallization charge vat 50 by a line 53a. The obtained crystals, saturated with mother liquor, are sent by a line 54 into at least one partial melting zone 55 which is used at a temperature of about 10° C. The proportion of crystals in the partial melter can be controlled by the recycling of a portion of a washing liquor described below and introduced by a line 58a and by an input of calories by any suitable means. By a line 56, a new crystal suspension is recovered which is introduced into at least one NIRO-type washing column 57, into which a washing solvent is introduced countercurrent to the intake of the suspension, by a line 60b. Pure paraxylene crystals in suspension are recovered coming out of the column by a line 59, and are completely melted in at least one melter 61 which delivers a liquid stream of very pure paraxylene by a line 60. A portion of this liquid paraxylene can be introduced as washing solvent into column 57 by a line 60b. Finally, collected from column 57, by a line 58, is a washing liquor which is recycled at least in part in crystallizer 50, another portion being able to be recycled by a line 58a to partial melter 55.

According to a variant of this device, when at least one centrifuge (pusher-type, for example) is used instead of countercurrent washing column 57, in general a centrifuge 52 is recommended in which a washing of crystals of the suspension is performed at the output of crystallizer 50 by means of a portion of the washing liquor introduced by a line 58b, shown in dotted line, which is collected from centrifuge 57.

According to another variant illustrated by FIG. 3 with the same references as those of FIG. 2, and which uses a washing solvent other than the melted paraxylene of high purity and that is lighter than it, such as toluene, the suspension of crystals coming out of partial melting zone 55 is separated and washed with toluene introduced by a line 66 and recycled toluene. Actually, the stream of melted paraxylene containing toluene that is distilled in a distillation column 63 is collected coming out of melter 61 by line 60. On the one hand, liquid paraxylene of very high purity is collected by a line 60b, and, on the other hand, toluene that is recycled in washing column 57 or in centrifuge 57, where the washing is performed, is collected by A line 62. The washing liquor collected by line 58, which also contains solvent, is introduced into another distillation column 64, then recycled as described above. The recovered solvent is also recycled in washing zone 57 by a line 65.

Figure 4:
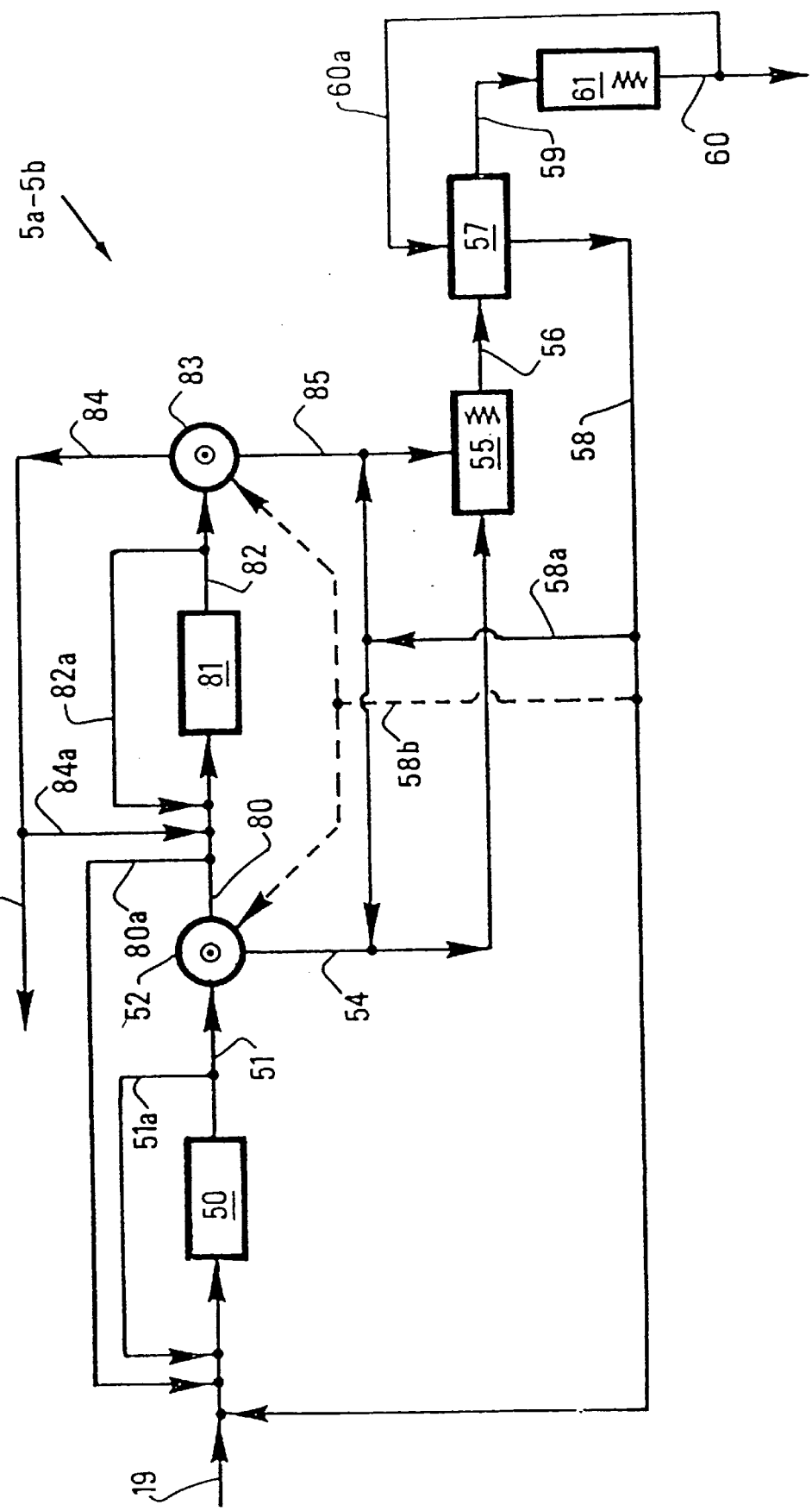
FIG. 4 shows the purification of paraxylene by crystallization in a double stage at high temperature.

FIG. 4 illustrates a variant of the purification (zones 5a, 5b) of the paraxylene at several stages of crystallization. The same elements as those of FIG. 2 with the same functions are referenced with the same numbers.

The suspension of first crystals coming out of first crystallization stage 50, whose temperature T1 is about 0° C., is introduced by line 51 into at least one centrifuge 52. The first crystals thus separated are sent by line 54 into partial melting zone 55 where at least a portion of the smallest crystals are melted. The mother liquor coming out of centrifuge 52 is at least in part/introduced by a line 80 into at least a second crystallizer 81 operating at a temperature T2 equal to about −18° C. A portion of this mother liquor can be recycled by a line 80a into the first crystallizer to maintain a crystal proportion there at about 30%. A suspension of second crystals in a second mother liquor is recovered by a line 82 and introduced at least in part into at least a second centrifuge 83, the other portion of the suspension optionally being recycled into second crystallizer 81 by a line 82a. On the one hand, a second mother liquor that is recycled at least in part to adsorption zone 8 by lines 84 and 3 is collected by a line 84 connected to the centrifuge. A portion of this second mother liquor can be recycled by a line 84a into the second crystallizer to maintain about 30% crystals in the effluent. On the other hand, second crystals saturated with mother liquor are recovered from the centrifuge by a line 85 and are introduced in partial melting zone 55 which is, according to FIG. 4, common to the first and to the second paraxylene crystals. All of the small-sized crystals are generally melted and a new suspension of crystals (line 56), whose proportion of solids is about 35%, can be adjusted by a portion of washing liquor 58a introduced in lines 54 and 85 which respectively bring the first and second crystals. This new suspension of crystals is separated and washed as has been mentioned above, for example, in washing column 57 into which melted paraxylene of very high purity coming from complete melting zone 61 has been introduced countercurrent by line 60a. The washing liquor is recycled at least in part by line 58 and can be mixed with the charge of the first crystallization.

When washing zone 57 is a pusher-type centrifuge, for example, a portion of the washing liquor can be recycled by a line 58b, shown in dotted line, to first centrifuge 52 and/or second centrifuge 83. Furthermore, the paraxylene crystals are collected by line 59.

Furthermore, when the washing solvent is a solvent other than the melted paraxylene, the device requires, as has been described above (FIG. 3), a distillation of the melted paraxylene coming out of melter 61 to obtain, for example, 99.9% purity and a distillation of washing liquor 58 making it possible to recycle the washing liquor essentially without solvent in various recycling lines 58a, 58b and 67 (FIGS. 3 and 4).

It has been found finally that the countercurrent washing in a column was more advantageous than the washing in a centrifuge. Actually, with equal paraxylene purities, the washing in a centrifuge requires intermediate washings as well as a partial melting step at higher temperature, which involves the production of a larger amount of washing liquor to be recycled in the crystallizers, therefore an increased heat exchange surface and an increased consumption of cold energy, as well as a larger number of centrifuges.

Furthermore, the process including a column washing accepts charges of very variable overall compositions, for example 85 to 95% paraxylene coming out of the enrichment zone, without significant modifications of equipment.

As has been diagrammed in FIG. 1, the mother liquor coming from crystallization unit 5a, 5b is recycled to adsorption unit 8. In the case of a two-stage crystallization, the mother liquor comes from the coldest crystallization stage after the separation of the paraxylene crystals (line 84, FIG. 4). The impurities which circulate in the loop of the adsorption, crystallization, isomerization device can be olefinic hydrocarbons, as well as paraffinic and naphthenic hydrocarbons or other oxygenated compounds. They can come in particular both from the charge to be treated which comes from a catalytic reforming and from the isomerization. These impurities therefore circulate and can be found in all the fractions and particularly in the extract and therefore in the mother liquor resulting from the crystallization step. This mother liquor can be introduced by a line 32 that is connected to line 3 and to line 84 (FIG. 4) in at least one clay-treatment reactor 26, advantageously two, placed upstream and connected by a line 27 to the adsorption unit. Line 1 containing the charge to be treated and line 2 containing the isomerate can be connected to this line 32, the three flows being thus treated in a mixture in the reactor 26.

According to another variant, charge 1 can have been pretreated in another clay treatment reactor (not indicated in the figure). It is the same for isomerate 2 which can also have been initially pretreated after having passed into distillation unit 23.

According to a preferred variant, mother liquor 3 can be introduced directly into line 22 leading to distillation unit 23 of the isomerate, before being treated, in mixture with the distilled isomerate, in clay treatment reactor 26. This variant makes it possible to eliminate approximately all the most volatile compounds, not only from the isomerate but from the mother liquor.

When the distillation unit is adjusted to deliver also, at the bottom, an additional fraction containing most of the heavy compounds (C9+hydrocarbons, aldehydes, ketones), the clay treatment of the distilled mixture comprising the isomerate and the mother liquor is thereby substantially improved.

A portion of the mother liquor can also be recycled by a line 31 to effluent 27 of reactor 26.

The effluent of the clay-treatment reactor and optionally crystallization mother liquor 31 that can further contain heavy hydrocarbons, such as hydrocarbons having nine carbon atoms, are introduced by a line 27 into a distilling column 28 which delivers, at the bottom of the column (line 29), the undesirable impurities and, at the top, a distillate corresponding to the purified $C_8$ fraction, that is introduced by line 4 to adsorption unit 8. A portion of the mother liquor can also be introduced into line 4 by a line 30.

These various recyclings can be combined with one another, when it involves, for example, reusing existing pieces of equipment for distillation 23, clay treatment 26 or distillation 28 and when one of these pieces of equipment is already operated at its maximum flow rate or else when it is desired to have the amount of an impurity in the loop lowered without seeking to eliminate it completely. In other words, the mother liquor of the crystallization unit (the coldest stage), conveyed by line 3, can be partially recycled to adsorption unit 8 either directly by means of line 30, or indirectly by means of lines 31, 32 or 33.

So as to keep the amount of constituents with intermediate volatility between the toluene (desorption solvent) and the xylenes, at a tolerable level, for example less than 5%, at least one purge of toluene polluted by said constituents is performed by means of a line 35 connected either to line 17, or to line 14 or to line 11 collecting all the solvent recycled to adsorption unit 8.

In addition, it is possible to perform a purge of a portion of the mother liquor coming from the crystallization if the amount of constituents with intermediate volatility is too great there. This purge is performed by means of line 34 connected to line 3.

The purge of toluene can be compensated for by an added portion of toluene. Since the greatest sources of $C_8$-aromatic fraction (line 1a) come from catalytic reforming, from dismutation (disproportionation) of the toluene into benzene and xylene and from the toluene-$C_9$-aromatic transalkylation and since the effluents of these units from which they come are in part generally purified in a series of distillation units of which column 28 can be a part, it is possible to use, at least in part, as a source of added portion of toluene, either the one produced at the top (line 42) of a distilling column of toluene 40, before reactor 26 containing the clay, or the one which results from the bypass by a line 1b of at least a portion of the charge (line 1a) that is mixed with effluent 41 from the bottom of column 40, or the one which is introduced into the purified charge (line 1) by putting column 40 out of adjustment, which makes it possible to allow the desired proportion of toluene to pass into the $C_8$ fraction.

EXAMPLES

The invention is illustrated by the following example:

The crystallization charge (10 T/h) according to FIG. 4 contains 88.5% by weight of paraxylene and is sent into the first crystallization stage and cooled to 2° C. with a recycling of a portion of washing liquor (2.7 T/h), a recycling of the suspension of first crystals (127 T/h) and of first mother liquor (13.1 T/h). The first crystals obtained after separating from the first suspension of crystals are put into suspension with a portion of the washing liquor (10 T/h) and sent to the partial melting vat. The first mother liquor is introduced in the second crystallization stage and cooled to −18° C., at the same time as a second recycled mother liquor (3.7 T/h) and a recycling stream of the suspension of second crystals (41.7 T/h). After centrifuging, on the one hand, a second mother liquor stream (5.7 T/h) with 43.9% by weight of paraxylene, 2 T/h being recycled to the adsorption, and, on the other hand, second crystals which are put into suspension with another portion of the washing liquor (3.1 T/h) are recovered and sent to the partial melting vat, whose temperature is maintained at 7° C.

The suspension of crystals coming from the partial melting vat is washed in a countercurrent washing column using melted paraxylene as a washing solvent, so as to recover 15.8 T/h of washing liquor and 8 T/h of paraxylene at 99.9% purity.

What is claimed is:

1. A process for the production of paraxylene from a charge containing a mixture of aromatic hydrocarbons having 7 to 9 carbon atoms, wherein at least a part of the charge is circulated in a zone enriching a first fraction to at least 30% by weight of paraxylene, and at least a portion of said first fraction is purified by at least one high-temperature crystallization in a least one crystallization zone, the process comprising:
   a) crystallizing said first fraction enriched with paraxylene in a crystallization zone at temperature T1,
   b) recovering from said crystallization zone crystals in suspension in a mother liquor,
   c) separating the crystals of the mother liquor in a least a first separation zone,
   d) partially melting the crystals obtained in at least one partial melting zone to produce a suspension of crystals,
   e) separating the crystals in suspension of (d) and washing said crystals with a washing solvent in at least one separating and washing zone, recovering pure paraxylene crystals, and a washing liquor; and
   f) optionally completely melting said pure crystals and collecting a liquid stream of melted paraxylene.

2. The process according to claim 1, wherein the paraxylene-enrichment zone is at least one crystallization zone operated at very low temperature, said process comprising introducing to said crystallization zone the charge containing a mixture of hydrocarbons having 8 carbon atoms and separating therefrom a liquid, isomerizing said liquid in an isomerization zone to produce crystals, and melting said crystals to produce at least a portion of said first fraction.

3. The process according to claim 1, wherein the paraxylene-enrichment zone is a selective adsorption zone containing a zeolitic adsorbent, said process comprising selectively adsorbing the charge containing a mixture of hydrocarbons having 8 carbon atoms in said zone in the presence of a desorption solvent, recovering said first paraxylene-enriched fraction and a second paraxylene-depleted fraction, isomerizing said second fraction in an isomerization zone containing a catalyst for isomerization under conditions suitable for producing an isomerate that is richer in paraxylene, and recycling the isomerate at least in part to the adsorption zone.

4. The process according to claim 1, wherein at least a portion of mother liquor resulting from c) is recycled to the zone enriching the first fraction.

5. The process according to claim 1, wherein the paraxylene enrichment zone is at least one zone of disproportionation of a charge consisting essentially of toluene, producing an effluent containing benzene and xylenes, said process comprising distilling said effluent to remove benzene and unreacted toluene.

6. The process of claim 1, comprising crystallizing at least a portion of the mother liquor resulting from c) in a second crystallization zone at a temperature T2 that is lower than temperature T1 of crystallization zone of a), recovering second crystals in suspension in a second mother liquor, separating said second crystals in a second separation zone, partially melting the second crystals in at least one zone for partial melting, recovering a suspension of said first crystals resulting from d) and second crystals, separating and washing the crystals in suspension in at least one zone for separating and washing with the washing solvent, recovering pure paraxylene crystals, and a washing liquor, and optionally completely melting said pure crystals and collecting a liquid stream of melted paraxylene.

7. The process according to claim 1, wherein at least a portion of washing liquor is recycled to the crystallization zone.

8. the process according to claim 1, wherein a portion of washing liquor is recycled to the zone for partial melting.

9. The process according to claim 6, wherein at least a portion of second mother liquor is recycled to the adsorption zone or to the second crystallization zone.

10. The process according to claim 6, wherein a portion of second mother liquor is recycled to the second crystallization zone.

11. The process according to claim 1, wherein the zone for separating and washing is at least one countercurrent washing column into which at least a portion of a liquid stream of melted paraxylene is introduced as a washing solvent.

12. The process according to claim 1, wherein the zone for separating and washing is a column for countercurrent washing by a solvent other than purified paraxylene, said process further comprising separating washing solvent from pure paraxylene crystals in suspension coming from said column in at least one centrifuge or one filter, completely melting the crystals and recycling the washing solvent in the column.

13. The process according to claim 1, wherein the zone for separating and washing is at least one centrifuge or one rotary filter, and a portion of a liquid stream of melted paraxylene is introduced therein as washing solvent.

14. The process according to claim 1, wherein the washing solvent is a solvent other than paraxylene, said process further comprising distilling the stream of melted paraxylene to recover liquid paraxylene of very high purity and washing liquor, recycling said washing liquor at least in part to the zone for separating and washing, distilling the washing liquor and recycling at least a portion of distilled washing solvent to the zone for separating and washing.

15. The process according to claim 1, wherein the zone for separating and washing comprises at least two separation zones and is at least one centrifuge or one rotary filter and wherein a portion of the washing liquor is recycled to a first separation zone.

16. The process according to claim 6, wherein the zone for separating and washing comprises at least two separation zones and is at least one centrifuge or one rotary filter and wherein a portion of the washing liquor is recycled to a second separation zone.

17. The process according to claim 6, wherein the partial melting zone of the first crystals and the partial melting zone of the second crystals are separate.

18. The process according to claim 6, wherein the temperature of the first crystallization zone is from +10 to −5° C. and the temperature of the second crystallization zone is from −5 to −25° C.

19. The process according to claim 6, wherein the temperature of the first separation zone is approximately constant and approximately equal to the temperature of the first crystallization zone.

20. The process according to claim 1, further comprising circulating at least a portion of the charge, a least a portion of the mother liquor, or at least a portion of the isomerate in at least one clay treatment zone, recovering a first effluent and introducing said effluent at least in part in the enrichment zone.

21. The process according to claim 1, further comprising introducing at least a portion of mother liquor into a distillation column downstream from the isomerization zone, distilling the isomerate and the mother liquor to obtain a top fraction containing light compounds and a second fraction containing a mixture of said distilled mother liquor and a distilled isomerate, introducing said second fraction into a clay treatment zone and recovering a second effluent.

22. The process according to claim 1, wherein T1 is +10 to −25° C.

23. A process for the production of paraxylene from a charge containing a mixture of aromatic $C_{7-9}$-hydrocarbons, comprising recovering paraxylene subsequent to a high temperature crystallization followed by partial remelting of paraxylene crystals to produce a suspension of crystals in melted paraxylene.

24. The process according to claim 23, further comprising separating the crystals from the suspension of crystals in melted paraxylene and washing the crystals with a washing solvent.

25. The process according to claim 23, wherein the crystallization is conducted at +10 to −25° C.

26. The process according to claim 23, comprising, prior to said high temperature crystallization, enriching the charge to at least 30% by weight paraxylene.

27. The process according to claim 8, wherein the recycling of the wash liquor to the partial melting zone is carried out upstream from said zone.

28. The process according to claim 8, wherein said recycle is heated.

29. The process according to claim 1, wherein the partial melting zone is operated at a temperature between the temperature of the crystallization zone and the melting temperature of the pure paraxylene.

30. The process according to claim 6, wherein the partial melting zone is operated at a temperature between temperature T1 and the melting temperature of the pure paraxylene.

31. The process according to claim 1, wherein the partial melting zone comprises a heater.

32. The process according to claim 1, wherein the slurry of d) contains about 35% of solids.

* * * * *